(12) United States Patent
Burton

(10) Patent No.: US 8,211,354 B2
(45) Date of Patent: Jul. 3, 2012

(54) BALLOON WITH INTEGRAL RETENTION OF A DILATION ELEMENT

(75) Inventor: David G. Burton, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 172 days.

(21) Appl. No.: 12/782,432

(22) Filed: May 18, 2010

(65) Prior Publication Data

US 2011/0288479 A1   Nov. 24, 2011

(51) Int. Cl.
*B29C 49/04* (2006.01)
*B29C 49/64* (2006.01)

(52) U.S. Cl. ............... 264/532; 264/535; 264/541

(58) Field of Classification Search ............. None
See application file for complete search history.

(56) References Cited

U.S. PATENT DOCUMENTS

| | | |
|---|---|---|
| 5,320,634 A | 6/1994 | Vigil et al. |
| 5,797,935 A | 8/1998 | Barath |
| 7,008,438 B2 | 3/2006 | O'Brien |
| 7,070,576 B2 | 7/2006 | O'Brien et al. |
| 7,153,315 B2 | 12/2006 | Miller |
| 7,396,358 B2 | 7/2008 | Appling et al. |
| 7,413,558 B2 | 8/2008 | Kelley et al. |
| 7,494,497 B2 | 2/2009 | Weber |
| 2004/0133223 A1 | 7/2004 | Weber |
| 2005/0015107 A1 | 1/2005 | O'Brien |
| 2005/0119678 A1 | 6/2005 | O'Brien et al. |
| 2005/0137615 A1 | 6/2005 | Mapes et al. |
| 2005/0137618 A1 | 6/2005 | Kunis |
| 2005/0149102 A1 | 7/2005 | Radisch, Jr. et al. |
| 2006/0184191 A1 | 8/2006 | O'Brien |
| 2007/0016278 A1 | 1/2007 | Shippy et al. |
| 2009/0234283 A1 | 9/2009 | Burton et al. |

OTHER PUBLICATIONS

PCT Written Search Report mailed Aug. 10, 2011, in related patent application No. PCT/US2011/036197 filed May 12, 2011.
"Use of a Cutting Balloon for Dilatation of a Resistant Venous Stenosis of a Hemodialysis Fistula," Dierk Vorwerk, Rolf W. Günther, Karl Schürmann, Heinz-Günther Sieberth; *Cardiovasc Interent Radiol* (1995) 18: 62-64.

*Primary Examiner* — Monica A Huson
(74) *Attorney, Agent, or Firm* — Brinks Hofer Gilson & Lione

(57) ABSTRACT

A balloon catheter is provided with integral channels for securing dilation elements to the outside of the balloon. The dilation elements have an anchor portion and an intermediate portion that are disposed within first and second longitudinal cavities in the channels. The balloon may be manufactured by extruding a parison and blow molding the parison with the dilation elements installed within the channels.

11 Claims, 4 Drawing Sheets

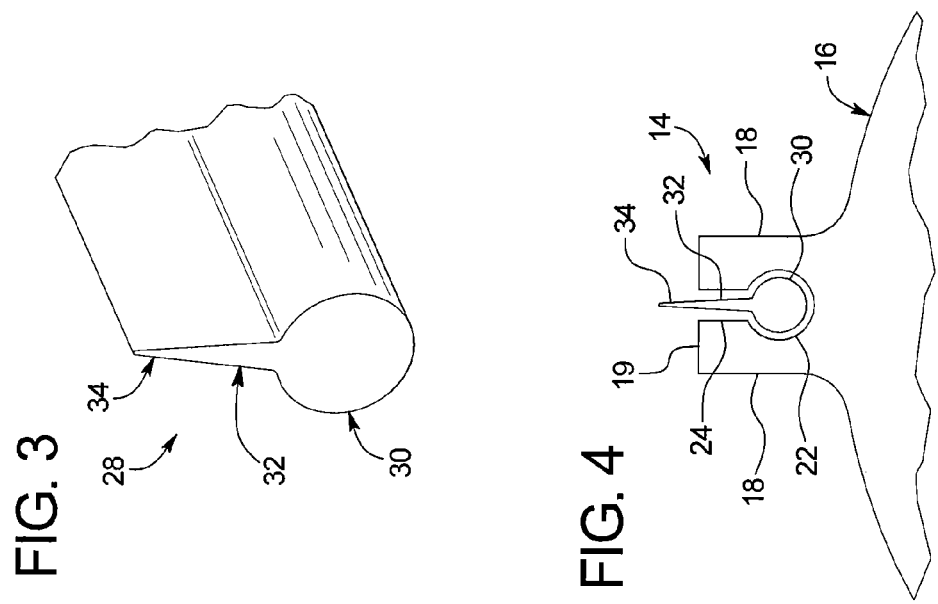
FIG. 1
FIG. 2
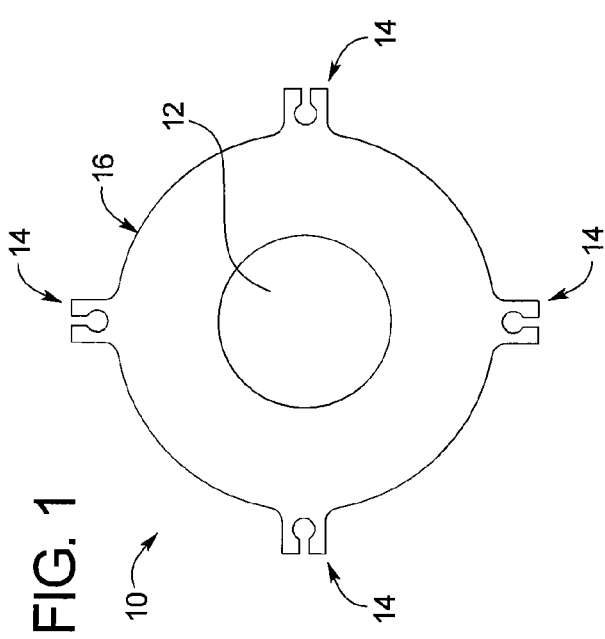
FIG. 3
FIG. 4

BALLOON WITH INTEGRAL RETENTION OF A DILATION ELEMENT

BACKGROUND

The present invention relates generally to medical devices and particularly to a balloon catheter with integral channels on the surface of the balloon for securing a dilation element.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, vascular angioplasty using a balloon catheter has drawn particular attention from the medical community because of the growing number of people suffering from vascular problems associated with arterial stenosis. This has lead to an increased demand for medical procedures to treat such problems. The widespread frequency of vascular problems may be due to a number of societal changes, including the tendency of people to exercise less while eating greater quantities of unhealthy foods, in conjunction with the fact that people generally now have longer life spans than previous generations. Angioplasty procedures have become a popular alternative for treating arterial stenosis because angioplasty procedures are considerably less invasive than other alternatives. As an example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for vascular treatments, the medical community has turned to angioplasty procedures, in combination with stenting and other procedures, to avoid the problems associated with traditional open surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the artery to be treated. During this stage, the balloon is uninflated and collapsed onto the shaft of the catheter in order to present a low profile which may be passed through the vasculature. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the body. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters. One solution that has been offered for dilating hardened stenoses is special balloon catheters with dilation wires or beads that extend along the length of the balloon. The dilation wires and/or beads focus that dilation pressure of the balloon onto the narrower contact area between the dilation wire or bead and the vessel wall. As a result, the increased, focused pressure may crack and/or break up the hardened stenosis, thereby allowing the vessel lumen to be expanded.

One approach that has been used to attach dilation wires and/or beads to a balloon is securing the wires and/or beads to the exterior surface of the balloon with adhesives. However, the use of adhesives to secure dilation wires and/or beads has several disadvantages. For example, there may be concern that the adhesive could detach from the balloon surface and allow the dilation wire and/or bead to break loose. This may be a particular concern when the adhesive is the only or the primary mechanism for securing the dilation wire and/or bead to the balloon surface. Detachment of the adhesive from the balloon surface can be a more serious problem when the balloon is made of a compliant or semi-compliant material, because the balloon material stretches as the balloon expands and the dilation wire and/or bead does not stretch during expansion or stretches at a different rate. Because of these opposing forces between the balloon material and the dilation wire and/or bead, the adhesive may crack or lose its adherence to the balloon surface. Moreover, even in the case of non-compliant balloons, detachment of the adhesive may be a concern because physicians are particularly adverse to any possible risk of intravascular device failures. Thus, a mechanism for more securely attaching dilation wires and/or beads to a balloon surface would be desirable.

In addition, the use of adhesives in a manufacturing setting is disadvantageous. Applying adhesives during the manufacturing process is typically a manually intensive task and time consuming. Maintaining cleanliness standards is also more difficult with the presence of adhesives, since adhesives are generally messy. The use of adhesives also requires extra fixturing to temporarily secure the parts being adhered while the adhesive cures.

Accordingly, the inventor believes it would be desirable to provide a balloon catheter with a mechanism that is integral with the balloon for securing a dilation wire and/or bead to the balloon surface.

SUMMARY

A balloon catheter is described that has integral channels along the length of the balloon for securing a dilation element to the balloon. The balloon may be made from an extruded parison with the channels integrally extruded with the parison. The dilation elements may be installed into the channels after the parison is extruded. The balloon may be formed by blow molding the parison.

The invention may include any of the following aspects in various combinations and may also include any other aspect described below in the written description or in the attached drawings.

A balloon catheter, comprising:
a balloon mounted on a catheter, the balloon configured to expand from a deflated state to an expanded state;
an integral channel disposed along a length of an exterior surface of the balloon, wherein the channel comprises a first longitudinal cavity and a second longitudinal cavity;
the first longitudinal cavity being larger in width than the second longitudinal cavity and being disposed nearer a longitudinal axis of the balloon than the second longitudinal cavity;
the second longitudinal cavity extending from the first longitudinal cavity to a longitudinal opening;
first and second longitudinal extensions extending from the exterior surface of the balloon and defining the first and second longitudinal cavities and the longitudinal opening, the first and second longitudinal extensions being integral with the balloon and opposing each other;
a dilation element comprising an anchor portion, an intermediate portion and a dilation portion, the anchor portion being larger in width than the intermediate portion; and
the anchor portion being disposed within the first longitudinal cavity, the intermediate portion being disposed within the second longitudinal cavity and the dilation portion extending outward from the longitudinal opening.

The balloon catheter wherein a first outer width across the first and second longitudinal extensions between the first longitudinal cavity and the exterior surface of the balloon is less than a second outer width across the first and second longitudinal extensions across the first longitudinal cavity.

The balloon catheter further comprising an integral third longitudinal extension extending between the first longitudinal cavity and the exterior surface of the balloon.

The balloon catheter further comprising an integral third longitudinal extension extending between the first longitudinal cavity and the exterior surface of the balloon.

The balloon catheter wherein the anchor portion comprises a generally flat portion adjacent the intermediate portion and a pointed end extending inward from the flat portion.

The balloon catheter wherein the anchor portion comprises a generally flat portion adjacent the intermediate portion, the flat portion having a generally constant thickness and defining a bottom of the dilation element.

The balloon catheter wherein the anchor portion is general circular.

The balloon catheter wherein a first outer width across the first and second longitudinal extensions between the first longitudinal cavity and the exterior surface of the balloon is less than a second outer width across the first and second longitudinal extensions across the first longitudinal cavity, and further comprising an integral third longitudinal extension extending between the first longitudinal cavity and the exterior surface of the balloon, wherein the anchor portion comprises a general flat portion adjacent the intermediate portion and a pointed end extending inward from the flat portion.

The balloon catheter wherein a first outer width across the first and second longitudinal extensions between the first longitudinal cavity and the exterior surface of the balloon is less than a second outer width across the first and second longitudinal extensions across the first longitudinal cavity, and further comprising an integral third longitudinal extension extending between the first longitudinal cavity and the exterior surface of the balloon, wherein the anchor portion is general circular.

A method of forming a balloon for a balloon catheter, comprising:
extruding a parison having a uniform shape along an entire length thereof, the parison comprising a central opening and first and second longitudinal extensions extending from an exterior surface of the parison and opposing each other, the first and second longitudinal extensions defining first and second longitudinal cavities and a longitudinal opening, wherein the first longitudinal cavity is larger in width than the second longitudinal cavity and is disposed nearer a longitudinal axis of the balloon than the second longitudinal cavity, the second longitudinal cavity extending from the first longitudinal cavity to the longitudinal opening;
disposing an anchor portion of a dilation element into the first longitudinal cavity, an intermediate portion of the dilation element being disposed within the second longitudinal cavity and a dilation portion of the dilation element extending outward from the longitudinal opening; and
heating the parison inside a mold and pressurizing the central opening, the parison thereby expanding against the mold, wherein the mold comprises a clearance cavity receiving the dilation portion.

The method further comprising stretching the parison while the parison is heated after the anchor portion is disposed into the first longitudinal cavity and before the parison is pressurized, the first longitudinal cavity thereby shrinking against the anchor portion and the second longitudinal cavity shrinking against the intermediate portion.

The method wherein the mold does not comprise any clearance cavities receiving the first and second longitudinal extensions along a tapered region extending to a neck region, the first and second longitudinal extensions thereby being compressed against the mold and substantially closing the first and second longitudinal cavities along the tapered region.

The method wherein the mold comprises a clearance cavity at least partially receiving the first and second longitudinal extensions along a neck region, the clearance cavity in the neck region thereby indexing the parison to the clearance cavity receiving the dilation portion.

The method further comprising disposing heat shrink tubing over the first and second longitudinal extensions along the neck region after the heating and pressurizing, the first and second longitudinal extensions along the neck region thereby being substantially reformed into the exterior surface of the parison.

The method wherein a first outer width across the first and second longitudinal extensions between the first longitudinal cavity and the exterior surface of the parison is less than a second outer width across the first and second longitudinal extensions across the first longitudinal cavity, the first outer width isolating the first and second longitudinal extensions during the heating and pressurizing to minimize reshaping of the first and second longitudinal extensions during the heating and pressurizing.

The method wherein the anchor portion comprises a generally flat portion adjacent the intermediate portion and a pointed end extending inward from the flat portion, the anchor portion being disposed into the first longitudinal cavity by pressing the anchor portion through the second longitudinal cavity.

The method wherein the anchor portion comprises a generally flat portion adjacent the intermediate portion, the flat portion having a generally constant thickness and defining a bottom of the dilation element, the anchor portion being disposed into the first longitudinal cavity by sliding the anchor portion through and open end of the first longitudinal cavity.

The method wherein the mold does not comprise any clearance cavities receiving the first and second longitudinal extensions along a tapered region extending to a neck region, the first and second longitudinal extensions thereby being compressed against the mold and substantially closing the first and second longitudinal cavities along the tapered region, the mold comprising a clearance cavity at least partially receiving the first and second longitudinal extensions along the neck region, the clearance cavity in the neck region thereby indexing the parison to the clearance cavity receiving the dilation portion, and further comprising disposing heat shrink tubing over the first and second longitudinal extensions along the neck region after the heating and pressurizing, the first and second longitudinal extensions along the neck regions thereby being substantially reformed into the exterior surface of the parison.

The method further comprising stretching the parison while the parison is heated after the anchor portion is disposed into the first longitudinal cavity and before the parison is pressurized, the first longitudinal cavity thereby shrinking against the anchor portion and the second longitudinal cavity shrinking against the intermediate portion.

The balloon wherein a first outer width across the first and second longitudinal extensions between the first longitudinal cavity and the exterior surface of the parison is less than a second outer width across the first and second longitudinal extensions across the first longitudinal cavity, the first outer width isolating the first and second longitudinal extensions during the heating and pressurizing to minimize reshaping of the first and second longitudinal extensions during the heating and pressurizing.

BRIEF DESCRIPTION OF SEVERAL VIEWS OF THE DRAWINGS

The invention may be more fully understood by reading the following description in conjunction with the drawings, in which:

FIG. 1 is an end view of an extruded parison;

FIG. 2 is an enlarged perspective view of a channel on the parison;

FIG. 3 is a perspective view of a dilation element;

FIG. 4 is an end view of the dilation element disposed within the channel;

DETAILED DESCRIPTION

Figure 5:
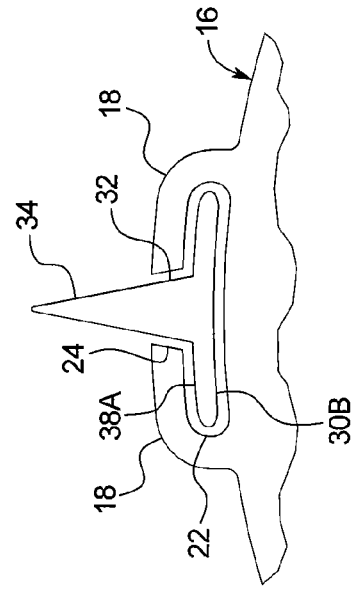
FIG. 5 is an end view of another dilation element and channel.

Referring now to the figures, and particularly to FIGS. 1-2, an extruded parison 10 is shown. The extruded parison 10 may be continuously extruded through a mold from a polymer material, such as nylon. Thus, each of the structures of the extruded parison 10 are integral with each other and extend along the entire length of the extruded parison 10. The extruded parison 10 may have a central opening 12 that is used for blow molding the parison 10 as described below. The central opening 12 will form the inner lumens of the neck regions 68, which are attached to a catheter 66, and will also form the interior of the balloon 64, which allows the balloon 64 to expand from a deflated state to an expanded state.

The extruded parison 10 also includes a channel 14 in the exterior surface 16 that extends longitudinally along the length of the extruded parison 10. The channel 14 includes two opposing longitudinal extensions 18 that extend outward from the exterior surface 16. At the other end 19, the space between the longitudinal extensions 18 defines a longitudinal opening 20. Between the longitudinal extensions 18 are first and second longitudinal cavities 22, 24 that also extend along the length of the parison 10. The second longitudinal cavity 24 connects the longitudinal opening 20 to the first longitudinal cavity 22. Thus, the first longitudinal cavity 22 is positioned inward from the second longitudinal cavity 24. The first longitudinal cavity 22 has a width that is larger than the width of the second longitudinal cavity 24. The bottom of the first longitudinal cavity 22 may also be spaced outward from the main exterior surface 16 of the parison 10 to form a third longitudinal extension 26 between the first and second longitudinal extensions 18 and between the bottom of the first longitudinal cavity 22 and the main exterior surface 16 of the parison 10. The third longitudinal extension 26 may also be thought of as a joined section of the first and second longitudinal extensions 18 at the base of the first longitudinal cavity 22.

As shown in FIG. 3, a dilation element 28 may also be provided. The dilation element 28 is preferably made from a different material than the extruded parison 10. For example, the dilation element 28 may be made of a metal to provide hardness and strength to the dilation element 28. The dilation element 28 includes an anchor portion 30, an intermediate portion 32 and a dilation portion 34. The width of the anchor portion 30 is larger than the width of the intermediate portion 32. The dilation portion 34 is designed to contact the vessel wall when the finished balloon catheter 66 is used to dilate a vessel passageway. As such, the shape of the dilation portion 34 may be designed for the particular application and may have a blade shape, bead shape or any other suitable shape for focusing pressure along a discrete longitudinal region.

As shown in FIG. 4, after the parison 10 has been extruded, the dilation element 28 is disposed within the channel 14 of the extruded parison 10. Specifically, the anchor portion 30 is positioned within the first longitudinal cavity 22, while the intermediate portion 32 is positioned through the second longitudinal cavity 24. The dilation element 28 may be positioned into the channel 14 by pressing the anchor portion 30 through the second longitudinal cavity 24 by flexing the top ends 19 of the first and second longitudinal extensions 18 outward. If the anchor portion 30 is too large to be pressed through the second longitudinal cavity 24 and/or the material of the parison 10 is too stiff to allow sufficient flexing of the first and second longitudinal extensions 18, the dilation element 28 may also be slid through the first and second longitudinal cavities 22, 24 from an open end of the cavities 22, 24. If additional securement of the dilation element 28 is desired, adhesive may be applied within the first or second longitudinal cavities 22, 24 to bond the dilation element 28 to the channel 14. However, it is preferred that no adhesive is used to bond the dilation element 28, since this would add extra cost and difficulty in manufacturing the balloon catheter 72. Although it is preferable for the dilation elements 28 to extend substantially the entire length of the working diameter region 74 of the balloon 64, it is also possible to use shorter dilation elements 28 that extend along only part of the length of the working diameter 74 of the balloon 64. In addition, while a single length of the dilation element 28 may be used along the length of the balloon 64, multiple dilation element sections 28 may also be used to provide flexibility to the finished balloon catheter 72.

Figure 6:
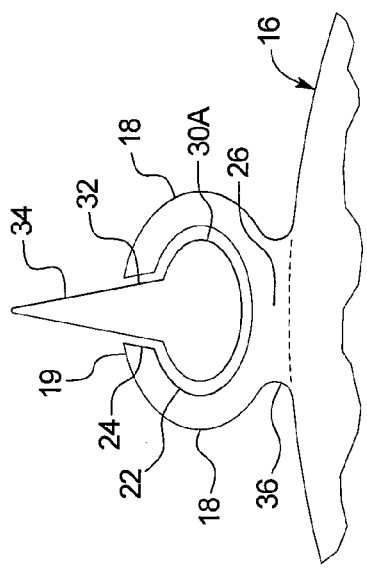
FIG. 6 is an end view of another dilation element and channel.
Figure 7:
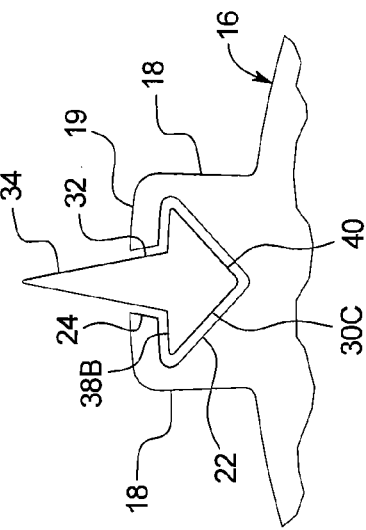
FIG. 7 is an end view of another dilation element and channel.
Figure 8:
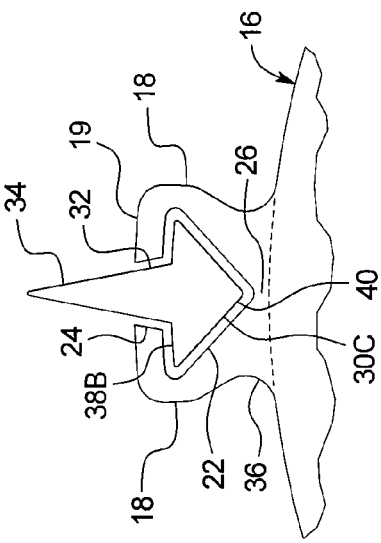
FIG. 8 is an end view of another dilation element and channel.

As shown in FIGS. 5-8, numerous variations of the integral channel and dilation element may be provided. As shown in FIG. 5, the anchor portion 30A may be circular in cross-section. The outer width across the first and second longitudinal extensions 18 is also narrower between the bottom of the first longitudinal cavity 22 and the exterior surface 16 of the parison 10 than it is across the first longitudinal cavity 22. In other words, the channel 14 has a narrowed neck region 36 below the first longitudinal cavity 22. As described further below, the narrowed neck region 36 may be useful to isolate the channel 14 during the blow molding process. As shown in FIG. 6, the anchor portion 30B may be thin and flat with a uniform thickness. Thus, in this design the bottom of the anchor portion 30B is generally flat. The generally flat anchor portion 30B preferably includes a slight arc shape that corresponds to the shape of the expanded balloon 64. The flat anchor portion 30B shown in FIG. 6 may provide improved anchoring since the flat portions 38A adjacent the intermediate portion 32 of the dilation element 28 are too wide to be pulled through the second longitudinal cavity 24. Because the anchor portion 30B cannot be easily pressed or pulled through the second longitudinal cavity 24, the dilation element 28 of FIG. 6 may be positioned into the channel 14 by sliding the anchoring portion 30B and intermediate portion 32 through an open end of the first and second longitudinal cavities 22, 24. As shown in FIGS. 7 and 8, the anchor portion 30C may have a generally flat portion 38B that is adjacent the intermediate portion 32 and may have a pointed end 40 at the bottom of the anchor portion 30C extending inward. This anchor portion 30C may have the advantage of being pressable through the second longitudinal cavity 24 since the pointed end 40 spreads the first and second longitudinal extensions 18. However, the flat portions 38B provide improved securement by making it difficult to pull the anchor portion 30C back through the second longitudinal cavity 24. As shown in FIG. 7, the channel 14 may be provided with a narrowed neck region 36 if desired. Alternatively, as shown in FIG. 8, the first and second longitudinal members 18 may extend straight down to the exterior surface 16 of the parison 10 without providing a narrowed neck region 36. One advantage of the non-circular anchor portions 30B, 30C shown in FIGS. 6-8 is that the anchor portion 30B, 30C itself can align the dilation portion 34 in the desired direction by the contact between the anchor portion 30B, 30C and the first longitudinal cavity 22. As a result, the portion of the first and second longitudinal extensions 18 above the second longitudinal cavity 22 may be minimized if desired. On the other hand, if a circular anchor portion 30A like FIG. 5 is used, the contact between the upper portions 19 of the first and second longitudinal extensions 18 and the intermediate portion 32 of the dilation element 28 may provide the necessary alignment of the dilation portion 34.

Figure 9:
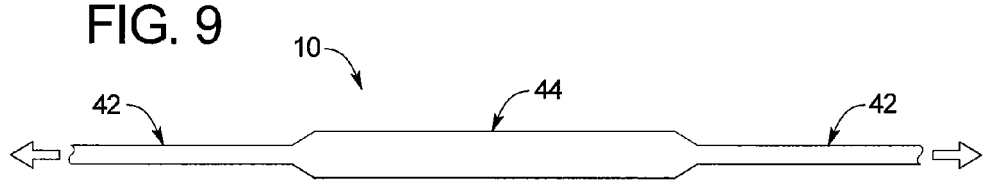
FIG. 9 is a side view of the parison being stretched.

As shown in FIG. 9, it may be preferable to initially stretch a portion 42 of the parison 10 before installing the dilation elements 28 into the channels 14 of the parison 10. The initial stretching process may be achieved by heating one end 42 of the parison 10 without heating the middle 44 of the parison 10. The heated end 42 of the parison 10 may be pulled to stretch it without causing the middle portion 44 to be stretched. The other end 42 may then be heated and stretched in a similar manner.

Figure 10:
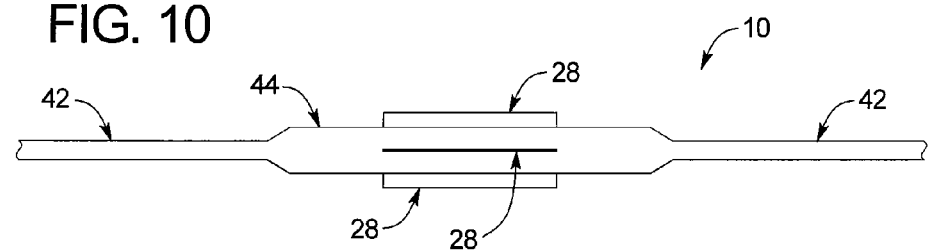
FIG. 10 is a side view of the parison with the dilation elements installed in the channels.

As shown in FIG. 10, the dilation elements 28 are then installed into the into the channels 14. As described above, this may be done by pressing the anchor portion 30 through the second longitudinal cavity 24 or may be done by sliding the anchor portion 30 and intermediate portion 32 through the first and second longitudinal cavities 22, 24 from an open end.

Figure 11:
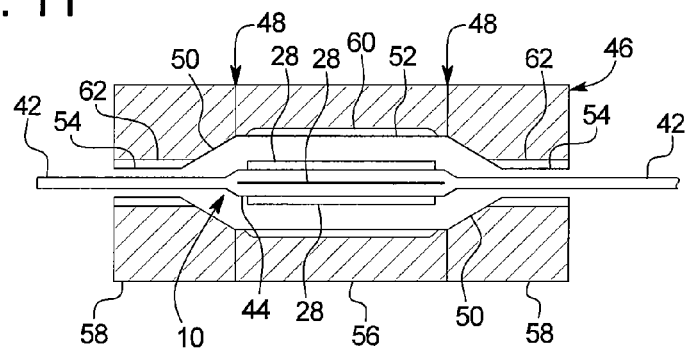
FIG. 11 is a side view of the parison in a mold.

As shown in FIG. 11, the parison 10 may then be positioned within a mold 46 for blow molding. While the mold 46 may take various forms, a three-piece mold 46 may be desirable. The three-piece mold 46 may be split in two places 48 at the transition between the tapered regions 50 and the working diameter 52. The parison 10 may be inserted into the mold 46 by separating one or more of the pieces of the mold 46 and inserting one end 42 of the parison 10 through one of the neck regions 54 in the mold 46. The working diameter piece 56 and/or the other neck piece 58 may then be slid over the other end 42 of the parison 10.

Figure 12:
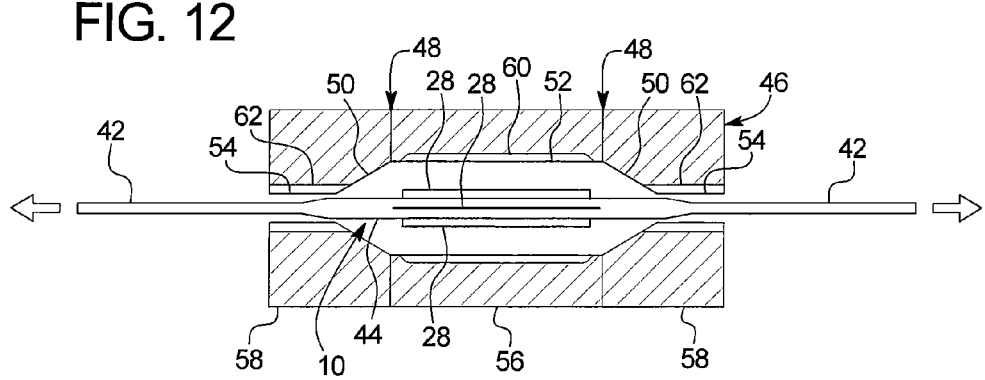
FIG. 12 is a side view of the parison in the mold and being stretched with the dilation elements installed.

As shown in FIG. 12, the parison 10 is preferably heated and stretched with the dilation elements 28 installed without pressurizing the center opening 12 prior to the blow molding. This is done by heating at least the middle portion 44 of the parison 10 and pulling on the ends 42 of the parison 10. Although a larger portion of the parison 10 may be heated, it may be desirable to only heat the portion of the parison 10 where the dilation elements 28 are installed and a small length beyond the ends of the dilation elements 28. The stretching of the middle portion 44 of the parison 10 causes the first and second longitudinal cavities 22, 24 to shrink in size and squeeze against the anchor portion 30 and intermediate portion 32 of the dilation elements 28. This locks the dilation elements 28 into the channels 14. The portions of the channel 14 that extend past the ends of the dilation elements 28 may also be partially closed by the stretching step. This can also result in longitudinally securing the dilation elements 28 within the channels 14.

The mold 46 may also have longitudinal clearance cavities 60 along the working diameter 52 that receive the dilation portion 34 of the dilation elements 28. If desired, the working diameter clearance cavity 60 may also receive the first and second longitudinal extensions 18 so that the channel 14 does not significantly contact the mold 46 during blow molding to avoid changing the shape of the channel 14. Alternatively, the working diameter clearance cavity 60 can be sized to contact the first and second longitudinal extensions 18 during blow molding to cause the channel 14 to be reformed into the final desired shape during blow molding. Preferably, the tapered regions 50 of the mold 46 do not have any clearance cavities to receive the first and second longitudinal extensions 18. As a result, when the parison 10 is blow molded, the channels 14 are compressed against the tapered regions 50 of the mold 46 and are closed and either mostly or entirely reformed into the wall of the finished balloon 64. The neck regions 54 of the mold 46 may or may not have clearance cavities for the first and second longitudinal extensions 18. However, it may be desirable to provide clearance cavities 62 that partially receive the channels 14 in order to index and align the parison 10 to the mold 46. The neck region clearance cavities 62 may be sized so that they partially reshape the channels 14 during blow molding to partially reform the channels 14 into the neck regions 68 of the balloon 64. Once the parison 10 has been indexed to the mold 46 so that the channels 14 are aligned with the clearance cavities 60, 62, the parison 10 is blow molded in the mold by heating the parison 10 and pressurizing the center opening 12. This causes the parison 10 to circumferentially stretch and expand outward against the walls of the mold 46. If it is desirable to minimize reforming and stretching of the channels 14 during blow molding, narrowed neck regions 36 as described above may be used to isolate the channels 14 from the main body of the parison 10 during blow molding.

Figure 13:
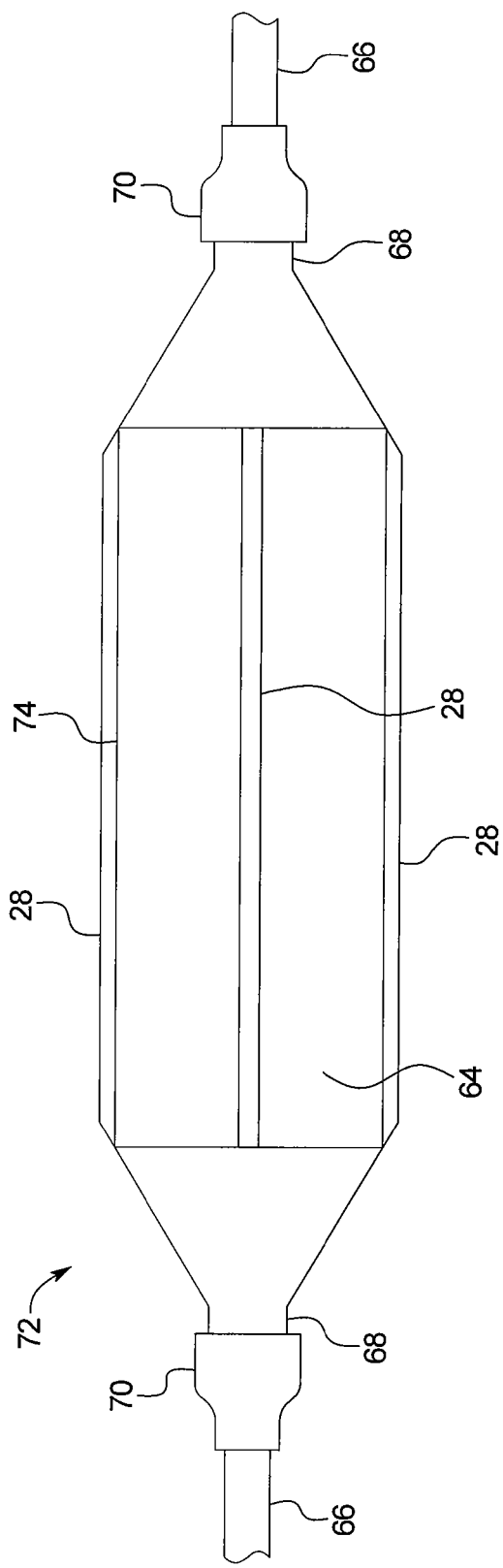
FIG. 13 is a side view of a balloon catheter with the dilation elements.

As shown in FIG. 13, after the parison 10 has been blow molded, the balloon 64 is cooled and removed from the mold 46. The balloon 64 is then mounted onto a catheter 66 by inserting the catheter 66 through the inner lumens of the neck regions 68 of the balloon 64. Preferably, the catheter 66 is bonded and sealed to the neck regions 68 of the catheter 66 by melt bonding. This may be accomplished by disposing heat shrink tubing 70 over the neck regions 68 of the balloon 64. The heat shrink tubing 70, neck regions 68 and catheter 66 are then heated. The heat softens the neck regions 68 and the catheter 66 and causes the heat shrink tubing 70 to shrink and squeeze the neck regions 68 and catheter 66 together. As a result, the neck regions 68 and catheter 66 melt together and adhere to each other when the heat shrink tubing 70, neck regions 68 and catheter 66 cool. In addition, the channels 14 are substantially reformed into the exterior surface of the neck regions 68 of the balloon 64 by the pressure of the heat shrink tubing 70 and the softening caused by the heat. This provides a smooth attachment between the catheter 66 and the balloon 64 without any significant remnant of the channels 14 in the neck regions 68.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A method of forming a balloon for a balloon catheter, comprising:
    extruding a parison having a uniform shape along an entire length thereof, said parison comprising a central opening and first and second longitudinal extensions extending from an exterior surface of said parison and opposing each other, said first and second longitudinal extensions defining first and second longitudinal cavities and a longitudinal opening, wherein said first longitudinal cavity is larger in width than said second longitudinal cavity and is disposed nearer a longitudinal axis of said balloon than said second longitudinal cavity, said second longitudinal cavity extending from said first longitudinal cavity to said longitudinal opening;
    disposing an anchor portion of a dilation element into said first longitudinal cavity, an intermediate portion of said dilation element being disposed within said second longitudinal cavity and a dilation portion of said dilation element extending outward from said longitudinal opening; and
    heating said parison inside a mold and pressurizing said central opening, said parison thereby expanding against said mold, wherein said mold comprises a clearance cavity receiving said dilation portion.

2. The method according to claim 1, further comprising stretching said parison while said parison is heated after said anchor portion is disposed into said first longitudinal cavity and before said parison is pressurized, said first longitudinal cavity thereby shrinking against said anchor portion and said second longitudinal cavity shrinking against said intermediate portion.

3. The method according to claim 1, wherein said mold does not comprise any clearance cavities receiving said first and second longitudinal extensions along a tapered region extending to a neck region, said first and second longitudinal extensions thereby being compressed against said mold and substantially closing said first and second longitudinal cavities along said tapered region.

4. The method according to claim 1, wherein said mold comprises a clearance cavity at least partially receiving said first and second longitudinal extensions along a neck region, said clearance cavity in said neck region thereby indexing said parison to said clearance cavity receiving said dilation portion.

5. The method according to claim 4, further comprising disposing heat shrink tubing over said first and second longitudinal extensions along said neck region after said heating and pressurizing, said first and second longitudinal extensions along said neck region thereby being substantially reformed into said exterior surface of said parison.

6. The method according to claim 1, wherein a first outer width across said first and second longitudinal extensions between said first longitudinal cavity and said exterior surface of said parison is less than a second outer width across said first and second longitudinal extensions across said first longitudinal cavity, said first outer width isolating said first and second longitudinal extensions during said heating and pressurizing to minimize reshaping of said first and second longitudinal extensions during said heating and pressurizing.

7. The method according to claim 1, wherein said anchor portion comprises a generally flat portion adjacent said intermediate portion and a pointed end extending inward from said flat portion, said anchor portion being disposed into said first longitudinal cavity by pressing said anchor portion through said second longitudinal cavity.

8. The method according to claim 1, wherein said anchor portion comprises a generally flat portion adjacent said intermediate portion, said flat portion having a generally constant thickness and defining a bottom of said dilation element, said anchor portion being disposed into said first longitudinal cavity by sliding said anchor portion through and open end of said first longitudinal cavity.

9. The method according to claim 1, wherein said mold does not comprise any clearance cavities receiving said first and second longitudinal extensions along a tapered region extending to a neck region, said first and second longitudinal extensions thereby being compressed against said mold and substantially closing said first and second longitudinal cavities along said tapered region, said mold comprising a clearance cavity at least partially receiving said first and second longitudinal extensions along said neck region, said clearance cavity in said neck region thereby indexing said parison to said clearance cavity receiving said dilation portion, and further comprising disposing heat shrink tubing over said first and second longitudinal extensions along said neck region after said heating and pressurizing, said first and second longitudinal extensions along said neck regions thereby being substantially reformed into said exterior surface of said parison.

10. The method according to claim 9, further comprising stretching said parison while said parison is heated after said anchor portion is disposed into said first longitudinal cavity and before said parison is pressurized, said first longitudinal cavity thereby shrinking against said anchor portion and said second longitudinal cavity shrinking against said intermediate portion.

11. The method according to claim 10, wherein a first outer width across said first and second longitudinal extensions between said first longitudinal cavity and said exterior surface of said parison is less than a second outer width across said first and second longitudinal extensions across said first longitudinal cavity, said first outer width isolating said first and second longitudinal extensions during said heating and pressurizing to minimize reshaping of said first and second longitudinal extensions during said heating and pressurizing.

* * * * *

UNITED STATES PATENT AND TRADEMARK OFFICE
CERTIFICATE OF CORRECTION

| | | |
|---|---|---|
| PATENT NO. | : 8,211,354 B2 | Page 1 of 1 |
| APPLICATION NO. | : 12/782432 | |
| DATED | : July 3, 2012 | |
| INVENTOR(S) | : David G. Burton | |

It is certified that error appears in the above-identified patent and that said Letters Patent is hereby corrected as shown below:

Column 10, claim 8, line 45, after "portion through" replace "and" with --an--.

Signed and Sealed this
Sixth Day of November, 2012

David J. Kappos
*Director of the United States Patent and Trademark Office*